United States Patent [19]

Zsolnay et al.

[11] 4,399,100
[45] Aug. 16, 1983

[54] AUTOMATIC PROCESS CONTROL SYSTEM AND METHOD FOR CURING POLYMERIC MATERIALS

[75] Inventors: Andrew Zsolnay, Manhattan Beach, Calif.; Kelly M. Perkins, Anchorage, Ak.; Leiv H. Blad, Van Nuys, CA

[73] Assignee: Lockheed Corporation, Burbank, Calif.

[21] Appl. No.: 220,369

[22] Filed: Dec. 29, 1980

[51] Int. Cl.³ .................. G06G 7/58; G01N 27/22; G01N 33/44

[52] U.S. Cl. .................. 422/62; 364/500; 422/109; 422/112; 422/131

[58] Field of Search .......... 422/131, 62, 109, 112; 23/230 A; 364/500, 496, 499; 436/55

[56] References Cited

U.S. PATENT DOCUMENTS

| | | | |
|---|---|---|---|
| 3,321,280 | 5/1967 | Trotter, Jr. et al. | 364/500 |
| 3,614,682 | 10/1971 | Smith | 364/500 |
| 3,791,792 | 2/1974 | Lindsay | 23/230 M |
| 3,846,073 | 11/1974 | Baum et al. | 422/62 |
| 3,878,379 | 4/1975 | Moody, Jr. et al. | 364/500 |
| 4,023,096 | 5/1977 | Schmidt | 23/230 A |

Primary Examiner—Michael S. Marcus
Attorney, Agent, or Firm—Frederic P. Smith

[57] ABSTRACT

The invention is directed to an apparatus and method for curing polymeric materials by use of a closed-loop, automatic process control technique. A dielectric monitoring device (15) senses the electrical characteristics which are analogous to viscosity changes taking place in an uncured or partially cured polymeric material (10) while heat is applied thereto. The generated analog signal, which changes in response to variations in the capacitance and dissipation of the polymeric material, is fed into a microcomputer (21) which determines from the direction and amplitude of the generated wave form both the maximum and minimum levels of capacitance and dissipation developed. When a predetermined condition is reached, the microcomputer (21) sends a control signal to processing equipment (24,25) to apply pressure, heat and/or vacuum to the polymeric material (10) at or near the onset of gelation but prior to the hardening point. The microcomputer (21) is programmed so as to discard random electrical signals and questionable data such as from short-term burst noises. The system can be used for curing various polymeric materials having differing characteristics.

6 Claims, 5 Drawing Figures

AUTOMATIC PROCESS CONTROL SYSTEM AND METHOD FOR CURING POLYMERIC MATERIALS

TECHNICAL FIELD

The invention relates to the field of process control and, in particular, to a system and method for automatic curing of polymeric materials.

BACKGROUND ART

The invention is generally related to systems for curing thermosetting polymeric materials and more particularly to apparatus and methods for curing resin-matrix composites. The curing of a thermosetting polymer composite, such as a precatalyzed, preimpregnated fibrous material (prepreg) typically involves: (1) temperature control to initiate and sustain polymerization and obtain the release of volatiles; (2) pressure control to assure proper compaction of the laminate, removal of voids and release of excess resin; and (3) vacuum control to enhance the removal of volatile materials. The proper control of the heat-up rate, the temperature gradient in the part, and the exact time at which pressure to consolidate the composite is applied are critical factors. Optimum mechanical properties in a cured composite are obtained when it is substantially void-free and has a proper resin/fiber ratio, i.e., in a preselected narrow processing range.

In the past, the curing of resin matrix composites has generally followed a fixed cure schedule or cycle, with the amount and rate of heat application and pressure application being predetermined by the method of using resin sampling techniques or small test specimens to determine the degree of curing and onset of gelation of the resin which takes place during a given cure cycle. The information gathered from the sampling process was then extrapolated to curing other like composites. Such sampling sometimes included the monitoring of the dielectric constant and dissipation (pseudo-viscosity) to aid in formulating a fixed cycle for applying pressure and vacuum to the composite during the pressure application window which occurs at the onset of gelation, as described in "In-Process Controlled Curing of Resin Matrix Composites", Michael J. Yokata, 22nd National SAMPE Symposium and Exhibition, Volume 22.

However, there are many inherent limitations in the present curing methods. For example, processes which are successful with small test panels often fail when extrapolated to full-size articles. Further, batch variations in the prepreg, slow polymerization (advancement) in storage, the presence of exothermic reactions, and variable processing equipment characteristics present unpredictable variables. In addition, cure requirements will change with the thickness of the composite and the degree of B-staging of the resin. Also, different schedules must be established for composites having differing resin systems or differing concentrations in a given resin system.

The prior art includes various attempts to obtain measurements of dielectric constants and other characteristics for use in controlling resin cures. The patent to Baum, et al, U.S. Pat. No. 3,846,073, discloses a resin curing apparatus wherein dielectric constant, pressure and temperature are measured for the purpose of controlling the polymer production. Temperature and pressure are adjusted in response to the developed data, but the process is not automated. The patent to Garst, U.S. Pat. No. 3,985,712, discloses an apparatus for the automatic control of resin curing. Batch temperature is periodically read and compared with previously empirically determined temperature-time characteristics which are stored in a memory. An apparatus for programmed dielectric constant testing is disclosed in the patent to Schmidt, U.S. Pat. No. 4,023,096. A capacitive sensor is revealed in the patent to Shawhan, U.S. Pat. No. 2,765,219. The sensor has a memory system which compares values of a variable during successive time intervals and provides a control depending on the nature of the variable.

None of the above prior art systems is satisfactory for achieving a completely cured resin composite having optimum mechanical properties. Accordingly, there is a need for a simple, efficient, reproduceable and accurate method for determining optimum times for applying temperature and pressure to a prepreg to insure optimum end results. Such method should preferably be automatic, have a flexibility capable of handling prepregs with different given characteristics, complete the curing process in the shortest feasible amount of time, and render a cured composite which is both substantially free of voids and which has a minimal resin content lying in a given acceptable range.

DISCLOSURE OF INVENTION

It is well known that thermosetting polymers used in advanced composite resin matrices are process sensitive, which can cause unacceptable variations in the mechanical properties of the end product. Curing describes the process by which thermosetting polymers are transformed from low-molecular weight oligomers to highly crosslinked molecular structures. To assure optimum mechanical properties of laminate products in a cured state, the cured composite must be substantially void-free, have a resin content within a narrow range and the laminae closely packed together.

Resin matrix composites are initially fabricated from a prepreg which consists of a matrix of uncured precatalyzed resin with reinforcing fibers. The prepreg generally has excessive resin therein, as well as the presence of volatiles, and has a relatively high viscosity at room temperature. As heat is applied during the curing cycle, the volatiles are driven off and the polymer slowly undergoes polymerization. With condensation-type polymers, such as phenolics, polyesters and condensation-type polyimides, a common reaction by-product is water. Addition-type polmers, such as epoxies and addition-type polyimides, on the contrary, do not generate appreciable amounts of moisture.

Although most polymers react via a number of transition states during curing, the complete chemical details of which are unknown, reaction rates are influenced by stereochemistry. The initial propagation of linear chains is rapid, since there is a greater probability of forming bonds between reactive sites. Since a water molecule is generated for each bond in condensation-type polymers, a profound drop in the dielectric constant (capacitance) accompanies this state. The reaction rate diminishes just prior to cross-linking between adjacent molecules, reflecting changed stoichiometry, along with the reduced probability of two reactive sites being in close proximity. With fewer water molecules being generated as a by-product, there is a rapid recovery in the dielectric constant, since water is being removed at a nearly constant rate throughout the remainder of the cure cycle. By sample monitoring of the dielectric constant, the degree of cure of the composite can be determined and this information can be used to develop a pressure/temperature application schedule. Such techniques are admittedly in the prior art.

Another parameter of the composite curing phenomena which can be monitored during the cure cycle is the dissipation (viscosity-related) which is a measure of the relative freedom with which dipoles respond to an alternating current field. In condensation-type polymer reactions, the dissipation gradually rises to a maximum, which is reached at or near the onset of gelation of the resin and then drops off rapidly until the resin hardens. With addition-type polymer reactions, the dissipation remains substantially constant until initiation of the cure cycle of the resin, at which time a short rise in dissipation takes place, after which it drops to its earlier level until shortly before gelation, at which time it rises rapidly to a second maximum point and then drops off to its initial level. Dielectric monitoring of the composite in order to signal variations in the dissipation for use in controlling the cure cycle has also been heretofore known.

Applicants' invention described herein is directed to providing a linking of a dielectric monitoring unit with a microprocessor and a temperature/pressure control unit to form an automatic closed-loop system. It has also been found that the desired time for applying pressure to condensation-type polymeric composites is during the time between the minimum reading of the capacitance and the second maximum point of capacitance, which later point is just prior to hardening of the polymer.

The major components of the automated in-process control system include a dielectric monitoring unit, a microcomputer with an associated computer program, a temperature control unit, and the processing equipment such as autoclaves or platen presses with associated pressure and/or vacuum regulation controls. State-of-cure signaling means and an operator real-time display unit can be included in the system.

In one embodiment of the invention, an uncured condensation-type resin is equipped with appropriate dielectric sensor probes. As the resin is heated in the processing equipment, it slowly undergoes polymerization. The dielectrometer monitors changes in the capacitance occurring between the probes and converts that information into an analog signal. The capacitance signal is periodically sampled and stored in the memory segment of the microcomputer. In accordance with the computer program, the stored values are compared by the microcomputer and the direction and amplitude of the analog wave form are determined. Random electrical signals and questionable data are discarded by a subroutine in the computer program.

The microcomputer essentially functions as a decision-maker interface between the raw input data and the control equipment. When a predetermined condition is reached, the microcomputer sends a signal to the processing equipment control unit, and/or other control units, such that pressure is applied to the composite at the most opportune moment of the cure cycle (the pressure application window).

The system provided herein proved to be reliable under a wide variety of laboratory conditions. The pattern-recognizing capabilities functioned with a high degree of reliability under (1) fast and slow heat-up rates, (2) the substitution of various resin systems, and (3) despite the existence of random electrical interference generated by nearby equipment.

BEST MODE FOR CARRYING OUT THE INVENTION

Figure 1:
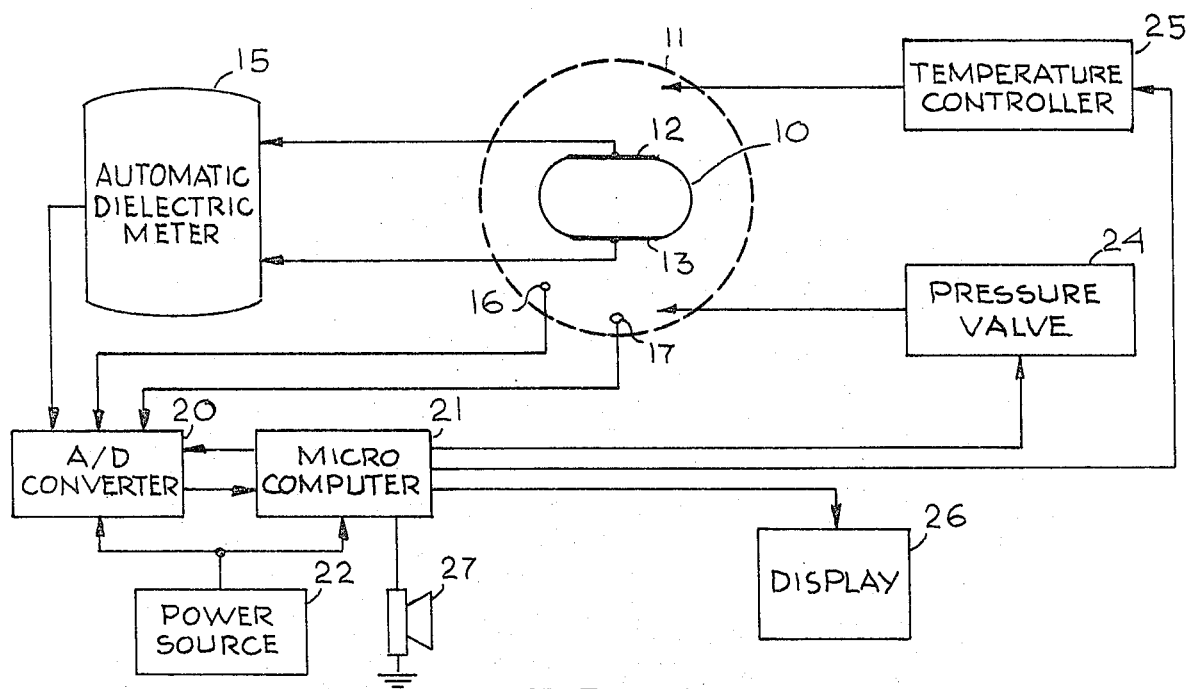
FIG. 1 is a schematic view of apparatus including a block diagram for performing the process of the invention for curing polymeric materials.
Figure 2:
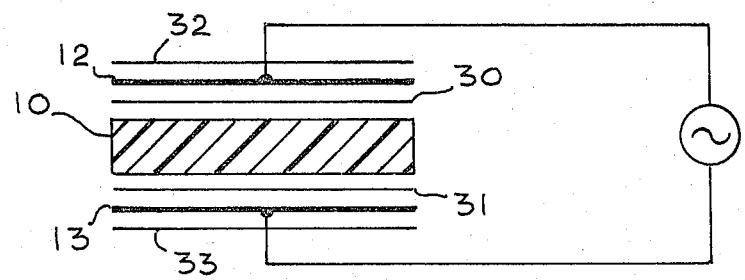
FIG. 2 schematically illustrates a polymeric material with electrodes applied thereto for providing capacitance and dissipation measurements.

Referring now to the drawings, and particularly to FIGS. 1 and 2, there is illustrated apparatus for performing a preferred embodiment of the process of the present invention. As shown in FIG. 1, the polymeric material 10 to be cured is contained in processing equipment 11. A pair of electrodes 12 and 13 are applied to the material 10 and are connected to an automatic dielectric meter 15. The meter 15 preferably is an automatic dielectrometry instrument known as an Audrey Dielectrometer, available from Tetrahedron Associates. It is capable of generating both a capacitance and a dissipation curve.

A temperature sensor 16 and a pressure sensor 17 are also contained in the chamber 11 close to the material 10. Signals obtained from the meter 15 and the sensors 16 and 17 are impressed upon an analog/digital converter 20. The converted signals are then impressed upon a microcomputer 21. Both converter 20 and computer 21 are energized by a power source 22.

The computer 21 generates a control signal which in turn controls a pressure valve 24 which may, for example, pressurize the processing equipment 11 for applying pressure to the material 10. Temperature controller 25 is adapted to receive signals from the computer 21 to control the temperature in the processing equipment 11. The computer 21 is also adapted to shut the system down in the event of excessive pressure and/or temperature being applied to the material 10. The computer 21 may also control a display device 26 as well as an acoustic warning device 27, such as a loud speaker.

FIG. 2 illustrates in greater detail one embodiment for providing alternating current voltage to the material 10 to generate the capacitance and dissipation curves. When composites having a resin system embedded in a glass matrix are employed, electrodes 12 and 13 can be disposed in direct contact with the composite. However, some composites also include oriented graphite fibers therein. Since graphite is conductive, it is necessary to provide some electrical insulation between the electrodes 12 and 13 and the material 10. Such insulation can consist of a pair of insulating layers 30 and 31 disposed between the material 10 and the respective electrodes 12 and 13, as shown in FIG. 2. The insulating material may consist of teflon-coated woven glass, or alternatively of a polyimide film or mica. The electrodes 12 and 13 themselves can consist of aluminum foil. Two more layers of insulative material 32 and 33 can be disposed respectively over the electrodes 12 and 13, such layers consisting, for example, of Kapton polyimide.

As noted previously, the time of applying pressure is quite critical to achieving an end product having optimum physical and mechanical properties. If the pressure is applied prematurely to a condensation composite, an excess of the resin is squeezed out and the resulting material is resin-poor. On the other hand, if the pressure is applied too late, hardening may have occurred and the excess resin cannot then be squeezed out resulting in a cured material which is resin-rich and too high in voids.

Figure 3:
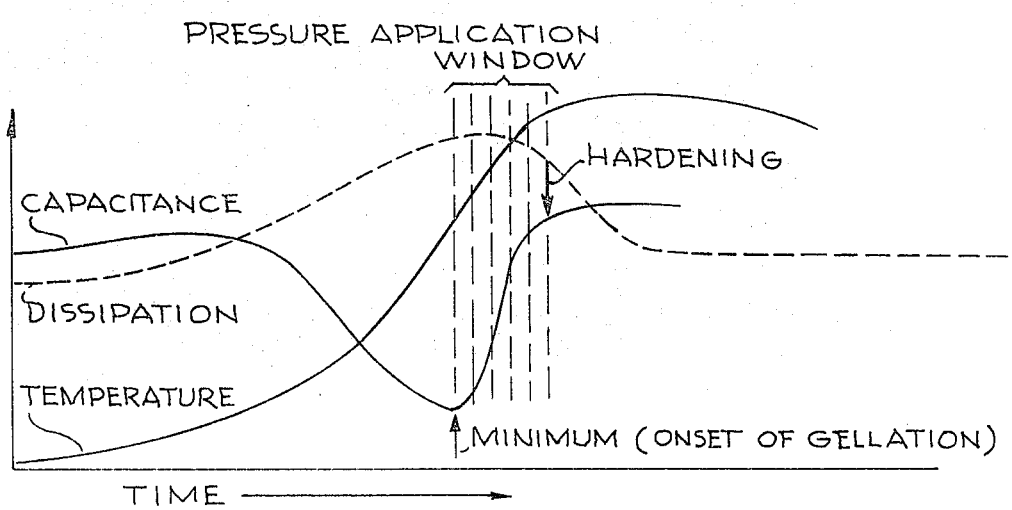
FIG. 3 is a graph illustrating relative changes in capacitance, dissipation and temperature measured as a function of time with a representative condensation-type polymer showing the pressure application window.

FIG. 3 illustrates the relative changes in capacitance, dissipation and temperature plotted as a function of time. These curves were developed by the apparatus shown in FIG. 1 with a composite consisting of a condensation-type polymer. It can be seen that as the temperature increases, the dissipation curve rises at a substantially constant rate to a maximum point during gelation of the resin and then diminishes concurrently with hardening of the resin. The capacitance initially rises to a maximum point. As the temperature increases, with attendant gradual polymerization of the resin, the capacitance gradually drops off to a minimum point reflecting the presence of condensation by-products (i.e. water) and then rises quickly back to a second maximum point. This rise takes place during the onset of crosslinking of the polymer, i.e., the onset of gelation. The time between this minimum point and the initial recovery of the curve, i.e., signaling the onset of gelation and hardening of the resin (pressure application window) has been found to be the optimum time to apply pressure to, for example, a platen press to squeeze out excess resin from the composite.

The prior art, as noted previously, has utilized dielectrometers to monitor capacitance and dissipation for use of such information by an operator to manually vary temperature and/or pressure application to the composite. However, in this type of conventional monitoring, problems have been encountered with short term impulse noise giving false minimum and maximum points. To overcome this problem, the present invention compares monitored values by means of a microcomputer manipulated slope tracking (analog to digital conversion) system which supplies data to a real time computer program for decision making.

The computer program of the present invention systematically obtains readings from the dielectric sensor, compares the reading to recently stored values, stores these readings and determines the resulting slope directions. Samples are obtained at program controlled intervals. Thus, errors that result from sampling too often are eliminated. By the selection of certain preset conditions, an operator is able to adjust the process to different types of polymer matrices and to receive status information by means such as a light emitting diode display. If desired, a fault warning system can be provided to allow operator notification if sampled parameters exceed maximum or minimum limitations.

A unique feature of the program is that short impulse noise from nearby electrical equipment is ignored by observing not one but several sample periods. The program basically is a series of sample, hold, wait, resample, compare and decision modules. The program establishes an initial zero slope value and proceeds to make an initial sample. Having sampled the dielectric reading of the resin under cure, the program compares and determines the slope trend.

The program in FIGS. 4a and 4b, for a condensation-type polymer reaction, tracks the slope trend until an initial maximum occurs, at which point an internal switch is set to reverse the slope direction, after which the controlled monitoring process resumes. Upon detection of the minimum capacitance value (inception of pressure window), the slope trend again reverses field toward a second maximum value. At that point, a decision switch acts to apply power to external pressure, vacuum and temperature controls, as desired.

The microcomputer system and program are uniquely qualified to perform the integrated function of trend monitoring and closed-loop control which have not been heretofore accomplished by other systems.

Figure 4:
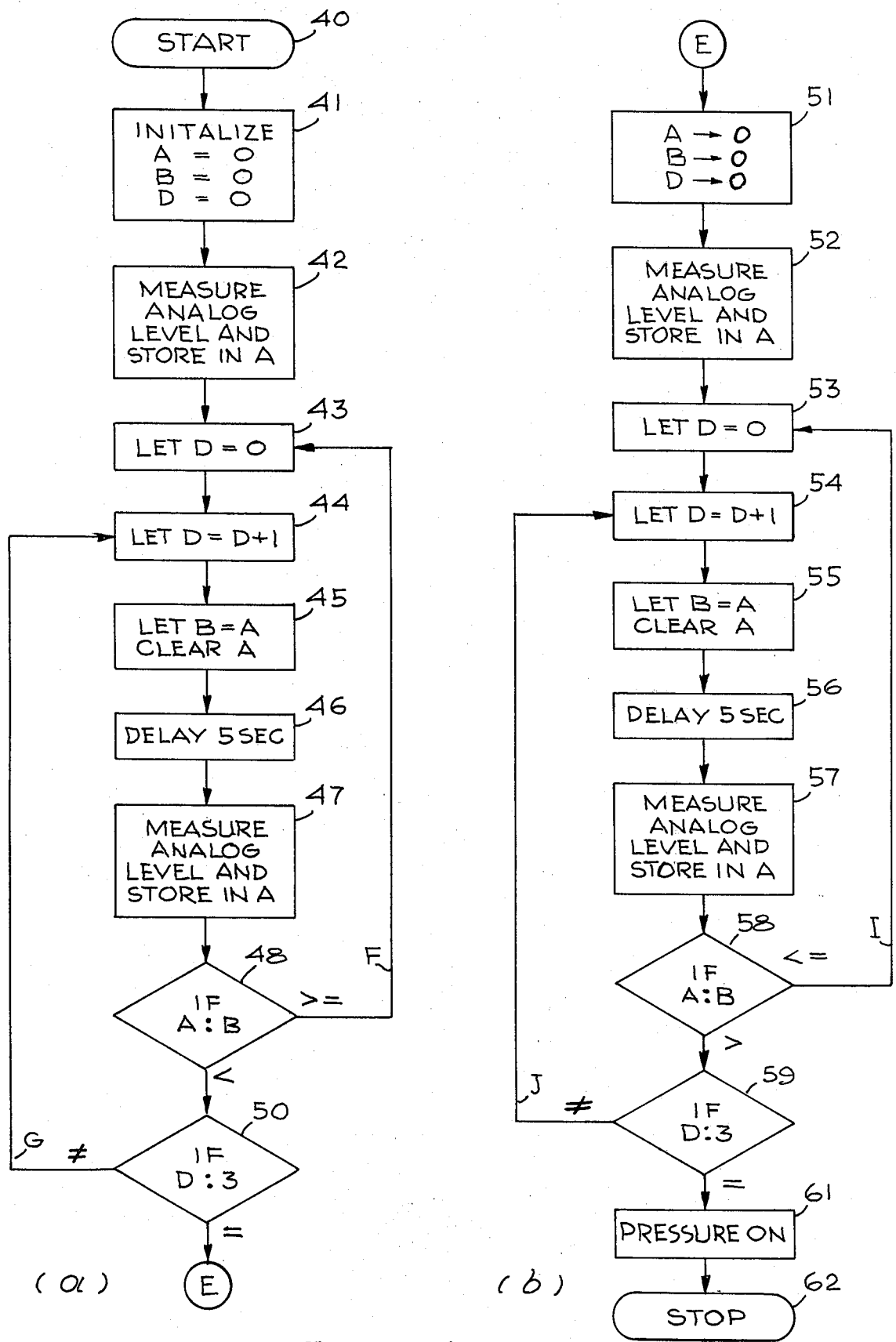
FIGS. 4a and 4b are flow charts of a computer program for developing a control signal to apply pressure to a condensation-type polymeric material.

FIG. 4 is a functional flow chart of a preferred computer program for implementing the above objects. As shown in FIG. 4a, the program starts as shown by box 40. The system is initiated as shown in box 41 by setting A, B, and D to zero to start the process. Both A and B are temporary storage devices, while D is a counter which counts the number of samplings. The analog level of the capacitance is measured as indicated at box 42 and the result is stored in A. In box 43 the counter D is again set to zero. In the next box 44, 1 is added to the counter D. Then, in box 45, B is made equal to A and A is cleared. In accordance with box 46, a time delay of five seconds is initiated. Thereupon, in box 47, the analog level is measured again and stored in A.

As shown in FIG. 4a and box 48, if A is greater than or equal to B, the information goes back to box 43, as shown by connection F, where the counter is set to zero again and the process repeats since a decreasing analog signal is being sought to establish a downtrend.

If A is smaller than B, that is, if the analog signal is decreasing, the process proceeds to box 50. Here another decision is made, namely, whether D is equal to 3 or unequal to 3. If it is unequal, the result goes back to box 44, as shown by connection G, where 1 is added to the counter D and the process repeats. The process is repeated to insure that the decrease is in fact true and not due to a short term variation causing a false signal.

If D equals 3, a downtrend of the curve is established, and the process continues to box 51 (FIG. 4b) where A, B and D are set to zero again. The next step taken, as shown by box 52, is to measure the analog level again and store it in A. In accordance with box 53, the counter D is set to zero, while in box 54, 1 is added to the counter D. As shown in box 55, the contents of memory A are then transferred to memory B while memory A is cleared. A delay of five seconds is again introduced by box 56 whereupon the analog level is measured again and stored in memory A (box 57).

In box 58, a comparison is made between A and B. If A is smaller than or equal to B, the information goes back to box 53 (connection I) where the counter is set to zero, and the process is repeated since an uptrend is now being sought. If A is greater than B, the process proceeds to box 59, where a decision is made whether D is equal to or unequal to 3. If D is unequal to 3, the process proceeds back to box 54 via connection J, 1 is added to the counter D and the process repeats. As before, the process is repeated to insure the increase is in fact true and not due to a short term variation causing a false signal.

Finally, if D does equal 3, an uptrend is established and a control signal is developed as shown by box 61 to apply the pressure (and activate other controls, if desired). The computer then stops, as shown at box 62.

It will now be seen that a downtrend is established when the computer reaches box 51 and an uptrend when it reaches box 61 with appropriate signals being given when such points are reached. Hence, the program reads the capacitance value in a manner which insures that a true downslope of the capacitance curve is first established, and subsequently establishes the initiation of a reversal to an upslope, thereby defining the minimum capacitance, which is the beginning of the optimum time for applying pressure to the composite. It is evident that the computer performs a slope-tracking operation. Thus, a program is provided which is inherently designed to ignore short term burst noise by the repeat operation controlled by boxes 50 and 59.

There has thus been disclosed a method for controlling curing of polymeric materials in general and of condensation-type polymeric materials in particular. Certain electrical characteristics, such as capacitance and dissipation, are monitored as a function of time by slope tracking. This makes it possible to generate a precise control signal at the optimum time, i.e., when the cross-linking is initiated, prior to the hardening point.

It is understood that other and different equivalent systems and programs can be utilized which are based upon and employ the inventive concepts set forth herein. Applicants intend only to limit the scope of their invention as such is defined in the appended claims.

INDUSTRIAL APPLICABILITY

The system and method is useful in the automatic curing of polymeric materials.

We claim:

1. An improved system for curing a polymeric material comprising:
   (a) heating means adapted to apply heat to said polymeric material;
   (b) pressure application means adapted to apply pressure to said polymeric material, said application of heat and pressure acting to cure said polymeric material;
   (c) dielectric monitoring means for measuring the capacitance of said polymeric material as said polymeric material is being cured and for generating a signal representative of said capacitance; and
   (d) computer means coupled to said monitoring means and said heating and pressure applications means for controlling the application of said heat and said pressure and for receiving said signal from said monitoring means and determining therefrom the optimum time to generate a control signal to apply to said pressure application means to cure said polymeric material, said optimum time occurring when said capacitance reaches a minimum value, said computer means including means for determining said minimum value of said capacitance measurements and means for generating said control signal immediately after said capacitance measurements pass through said minimum value.

2. The improved system of claim 1 wherein said computer means includes means for determining the maximum value of said capacitance measurements.

3. The improved system of claim 2 wherein said means for determining said maximum and minimum values includes means for tracking the slope of a curve formed from said capacitance measurements and determining whether the curve is in an upward or downward slope.

4. The improved system of claim 1 wherein said computer means includes means for disregarding false readings due to short-term impulse noise.

5. The improved system of claim 1 further comprising electrode means coupled to said monitoring means, said electrode means having said polymeric material disposed therebetween to measure the capacitance thereof.

6. The improved system of claim 5 further comprising insulating material disposed between said electrode means and said polymeric material.

* * * * *